United States Patent [19]

Oka et al.

[11] 4,279,997
[45] Jul. 21, 1981

[54] PROCESS FOR PRODUCTION OF AMINOGLYCOSIDE ANTIBIOTICS

[75] Inventors: Yoshihiko Oka, Kawagoe; Hitoshi Ishida, Ageo; Moto Morioka, Niiza; Yoso Numusaki, Ageo; Tsutomu Yamafuji, Tokyo; Takashi Osono, Tokyo; Hamao Umezawa, Tokyo, all of Japan

[73] Assignee: Yamanouchi Pharmaceutical Co., Ltd., Tokyo, Japan

[21] Appl. No.: 72,654

[22] Filed: Sep. 5, 1979

Related U.S. Application Data

[62] Division of Ser. No. 793, Jan. 3, 1979, Pat. No. 4,209,511.

[30] Foreign Application Priority Data

Jan. 13, 1978 [JP] Japan ................................. 53/3188

[51] Int. Cl.$^3$ ............................................ C12P 19/48
[52] U.S. Cl. ...................................... 435/80; 435/867
[58] Field of Search ............................................ 435/80

[56] References Cited

U.S. PATENT DOCUMENTS 3,982,996  9/1976  Daum et al. ............................ 435/80
4,045,298  8/1977  Nara et al. ............................ 435/80

Primary Examiner—Alvin E. Tanenholtz
Attorney, Agent, or Firm—Burgess, Ryan and White

[57] ABSTRACT

Aminoglycoside antibiotics biochemically transformed from Kanamycin A or Kanamycin B, which are represented by the formula

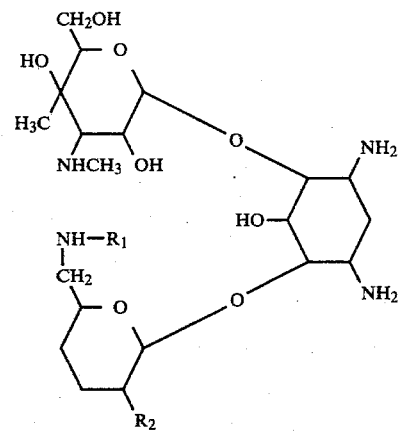

wherein $R_1$ represents a hydrogen atom or a methyl group and $R_2$ represents an amino group or a hydroxyl group.

4 Claims, 6 Drawing Figures

PROCESS FOR PRODUCTION OF AMINOGLYCOSIDE ANTIBIOTICS

CROSS-REFERENCE TO RELATED APPLICATION

This application is a division of co-pending application Ser. No. 793, filed Jan. 3, 1979, now U.S. Pat. No. 4,209,511 granted June 24, 1980.

BRIEF DESCRIPTION OF THE INVENTION

This invention relates to aminoglycoside antibiotics biochemically transformed from Kanamycin A or Kanamycin B, in more detail, aminoglycoside antibiotics represented by formula (I)

wherein $R_1$ represents a hydrogen atom or a methyl group and $R_2$ represents an amino group or a hydroxyl group, and a process for production thereof.

The compounds shown with formula (I) are novel compounds having chemical structures in which Kanamycins A and B have been deoxylated both at 3'- and 4'-positions, C-methylated at the 4''-position, and their amino group at the 3''-position has been methylated and their amino group at the 6'-position has optionally been methylated.

BACKGROUND OF THE PRESENT INVENTION

Hitherto, various aminoglycoside antibiotics have been known to be produced by a variety of microorganisms. It has also been known to obtain aminoglycosides having incorporated the added substances into the molecule by the use of mutants of these microorganisms and by addition of intermediates which these mutants can not produce, such as deoxystrepamine, neamine, or their analogs. [Proc. Nat. Acad. Sci., U.S.A., 63: 198–204(1969), J. Antibiot., 26: 784–786(1973), British Pat. No. 1,480,374, J. Antibiot., 29: 532–535(1976)].

Further, it has been known through the study of biosynthetic route of aminoglycosides that naturally occuring intermediates can be converted into the aminoglycoside when the intermediate is added to the culture of the same producing organism. [J. Antibiot., 28: 573–579(1975), J. Antibiot, 29: 140–146(1976)].

However, it has not yet been known that novel and useful aminoglycosides having modified main chemical structure of natural aminoglycosides can be obtained by the application of the biosynthetic pathway of microorganisms to afford biochemical transformation, such as the 3', 4'-dideoxylation and C-methylation at its monosacchride constituents, which have hitherto been available only by chemical synthetic route.

DETAILED EXPLANATION OF THE PRESENT INVENTION

Under these circumstances, the inventors of this invention have found that cultivation of Gentamicin-producing strains of Micromonospora species or their mutants in a medium containing Kanamycin A or Kanamycin B, known aminoglycoside antibiotics, provides novel compounds having a chemical structure as defined above in which Kanamycin A or Kanamycin B has been deoxylated at the 3'- and 4'-positions, C-methylated at the 4''-position, and their amino group at the 3''-position has been methylated and their amino group at the 6'-position has optionally been methylated, and they have also found that these novel compounds possess superior antibiotical activities to those of Kanamycins A and B.

Accordingly, the object of this invention is to provide novel and useful aminoglycoside antibiotics having general formula (I).

Another object of this invention is to provide a process for producing aminoglycoside antibiotics having general formula (I) or pharmacologically acceptable acid addition salts thereof which comprises cultivating Gentamicin-producing strains of Micromonospora species or their mutants in the presence of Kanamycin A or Kanamycin B.

The compounds of general formula (I) can further be converted into acid addition salts with pharmacologically acceptable nontoxic inorganic or organic acids, such as hydrochloric acid, sulfuric acid, phosphoric acid, acetic acid, propionic acid, stearic acid, tartaric acid, maleic acid, fumaric acid, aspartic acid, glutamic acid, etc. These salts can be obtained by lyophilization of their aqueous solution or crystallization from a water-miscible solvent. When they are aseptically prepared, they can be used for injection.

The compounds of general formula (I) possess broad antibacterial spectra, so they can be used for various purposes both in vivo and in vitro. For in vitro application, they can be used for sterilizing and disinfecting laboratory equipments and medical instruments, and for in vivo application, they are effective for treatment and prevention of various bacterial infections in animals including human beings.

The dosage of the compounds of general formula (I) may be modified according to varieties of diseases, ages and general condition of infected animals or patients, dosage forms of the preparation, etc. For example, in the case of human beings, the dose should be 0.04–1.0 g per day. The compounds are used in the form of tablets, capsules, powder, granules, syrup, dry syrup, aersols, suppositories or preferably injectable preparations.

The antibacterial activities (minimum inhibitory concentrations) of the compounds of general formula (I) are shown in the following table in comparison with Kanamycin A (hereinafter cited as KM-A), Kanamycin B (hereinafter cited as KM-B), Dibekacin (hereinafter cited as DKB) which is a chemical derivative of Kanamycin B, and Gentamicin C complex (hereinafter cited as GM-C) which have similar chemical structures to the compounds of general formula (I).

TABLE 1

| Microorganism | Minimum Inhibitory Concentration (Γ/ml) | | | | | | |
|---|---|---|---|---|---|---|---|
| | I-B$_1$ | I-B$_2$ | I-A$_2$ | GM-C | DKB | KM-A | KM-B |
| *Micrococcus flavus* ATCC 10240 | 0.39 | 0.39 | 0.78 | 0.39 | 3.13 | 6.25 | 1.56 |
| *Sarcina lutea* ATCC 9341 | 0.39 | 0.39 | 0.78 | 0.39 | 1.56 | 3.13 | 0.78 |
| *Staphylococcus aureus* Smith | 0.39 | 0.39 | 3.13 | 0.39 | 0.78 | 3.13 | 0.78 |
| *Mycobacterium phlei* | 0.78 | 0.39 | 1.56 | 0.78 | 1.56 | 1.56 | 3.13 |
| *Echerichia coli* NIHJ | 0.78 | 0.78 | 1.56 | 0.78 | 0.78 | 3.13 | 1.56 |
| *Salmonella enteritidis* 1891 | 0.78 | 0.39 | 1.56 | 0.78 | 0.78 | 3.13 | 1.56 |
| *Shigella sonnei* II 37148 | 0.78 | 0.78 | 3.13 | 0.78 | 1.56 | 3.13 | 1.56 |
| *Proteus vulgaris* OXK US | 0.78 | 0.78 | 3.13 | 0.78 | 1.56 | 6.25 | 6.25 |
| *Pseudomonas aeruginosa* ATCC 8689 | 3.13 | 3.13 | 6.25 | 3.13 | 1.56 | >100 | 100 |
| *Pseudomonas melanogenum* IAM 1655 | 1.56 | 1.56 | 6.25 | 1.56 | 1.56 | >100 | 50 |
| *Staphylococcus aureus* Onuma (PC-,SM-,Mao-resistant) | 0.19 | 0.19 | 3.13 | 0.19 | 0.19 | 1.56 | 0.78 |
| *Staphylococcus aureus* (PC-,SM-,TC-,KM-,Mac-resistant) | 0.19 | 0.19 | 6.25 | 0.19 | 0.19 | >100 | 50 |
| *Escherichia coli* K-12 ML-1629 | 1.56 | 1.56 | 3.13 | 1.56 | 1.56 | >100 | >100 |
| *Escherichia coli* K-12 R-5 | 1.56 | 25 | >100 | 1.56 | 100 | >100 | >100 |
| *Pseudomonas aeruginosa* 99 | 3.13 | 6.25 | 12.5 | >100 | 1.56 | 100 | 50 |
| *Pseudomonas aeruginosa* GN-315 | 1.56 | 50 | >100 | 6.25 | 100 | >100 | 100 |

(I-B$_1$: compound of Ex. 1, I-B$_2$: compound of Ex. 3, I-A$_2$: compound of Ex. 5)

As clearly understood from the table, the compounds of general formula (I) possess broad and strong antibacterial activities against various gram positive and negative bacteria, and show much stronger activity than those of Kanamycins A and B, that is the, starting materials. They also show potent antibacterial activities against Kanamycin A- and B-resistant *Escherichia coli* K-12 ML-1629 which inactivates aminoglycosides with a phosphotransferase, against Kanamycin A-, B- and Dibekacin-resistant *Escherichia coli* K-12 R-5 which inactivates aminoglycosides with an acetyltransferase, and against Gentamicin-resistant *Pseudomonas aeruginosa* 99 which inactivates aminoglycosides with an acetyltransferase. Accordingly, the compounds of general formula (I) concurrently possess the desirable properties of Dibekacin and Gentamicin. In acute toxicity test using compound (I-B$_2$) of Example 3, it was observed that mice tolerated a dose of 125 mg/Kg given intraveneously, at which dose Dibekacin and Gentamicin killed all the mice tested.

In view of the foregoing, the compounds of general formula (I) are considered to be superior to Gentamicin and Dibekacin and are very useful antibiotics as medicaments.

In this invention, the compounds of general formula (I) are obtained by cultivating Gentamicin-producing strains of Micromonospora species or their mutants in the presence of Kanamycin A or Kanamycin B.

Any strain can be used for this purpose if it can deoxylate the 3'- and 4'-positions of KM-A or KM-B, methylate the amino group at the 3''-position, C-methylate the 4''-position, and if desired, methylate the amino group at the 6'-position. As such strains, known Gentamicin-producing organisms, such as *Micromonospora echinospora* NRRL 2985(IFO-13149) and *Micromonospora purpurea* NRRL 2953(IFO-13150) are referred to, and Micromonospora sp. K-6993, belonging to a novel Micromonospora species, isolated by the inventors of this invention from a soil sample collected at Ishigaki island. Okinawa prefecture. Japan, and confirmed to produce Gentamicin.

Mutants can be obtained by treating Gentamicin-producing strains with conventional artificial mutagenic techniques, such as ultraviolet or X-ray irradiation, cobalt 60 irradiation, use of mutagenic agents, such as nitroso compounds, acridine pigments, nucleic acid base analogs, etc. Those mutants which show little or no Gentamicin production and can deoxylate and methylate KM-A and KM-B are preferred. As examples of such mutants, mutant strains designated Micromonospora sp. K-6993-Y-41 and *Micromonospora echinospora* NRRL 2985(IFO-13149)-N-6, which have been established by the inventors of this invention, can be cited.

The mycological properties of Micromonospora sp. K-6993, its mutant Micromonosora sp. K-6993-Y-41, and *Micromonospora echinospora* NRRL 2985 (IFO-13149)-N-6 are set forth as follows:

These strains have been deposited in American Type Culture Collection under depositing numbers of ATCC No. 31348, No. 31349 and No. 31350 respectively, and also deposited in the Institute of Microbial Industry, Agency of Industrial Science and Technology, Ministry of International Trade and Industry, Japan, under depositing numbers of FERM-P No. 4304, FERM-P No. 4305 and FERM-P No. 4303 respectively.

I. Morphological characteristics

The above-mentioned three strains have similar morphological appearance. They produce branched substrate mycelia, 0.5 to 1.0 microns in diameter, but have no aerial mycelia. On the top of each sporophore branching from substrate mycelia is produced a single spore, spherical or oval in shape. These strains grow well on Czapek agar and yeast extract-malt extract agar. The surface color of vegetative growth is usually purple on egg-albumin agar. Micromonospora sp. K-6993 and *Micromonospora echinospora* NRRL 2985(IFO-13149)-N-6 show similar mophorogical characteristics to *Micromonospora echinospora* NRRL 2985(IFO-13149). Micromonospora sp. K-6993-Y-41 shows poorer sporulation and paler vegetative growth compared with other two strains.

TABLE 2

|  | Micromonospora sp.K-6993 | Micromonospora sp.K-6993-Y-41 | Micromonospora echinospora NRRL 2985-N-6 |
|---|---|---|---|
| D-Glucose | ++ | ++ | ++ |
| D-Galactose | ± | + | − |
| D-Lactose | − | − | − |
| D-Mannitol | − | − | − |
| D-Xylose | ++ | ++ | ++ |
| D-Fructose | ± | ± | − |
| D-Arabinose | + | − | + |
| L-Arabinose | + | + | + |
| D-Raffinose | − | − | − |
| L-Rhamnose | − | − | ± |
| Sucrose | ++ | ++ | ++ |
| Starch | + | + | + |
| Glycerol | − | − | − |

| II. Cultural characteristics (at 29° C.) | | | |
|---|---|---|---|
|  | Micromonospora sp. K-6993 | Micromonospora sp. K-6993-Y-41 | Micromonospora echinospora NRRL 2985-N-6 |
| Czapek agar | Growth:good reddish purple orange to deep brownish black, no soluble pigment. | Growth:good, dull orange, no soluble pigment. | Growth:good, pale yellowishbrown to brownish black. no soluble pigment. |
| Glucose asparagine agar | Growth: poor, faint brownish-yellow, no soluble pigment. | Growth: poor, faint brownish-yellow, no soluble pigment. | Growth: poor, ochre, no soluble pigment. |
| Glycerol asparagine agar | Growth: none. | Growth: none. | Growth: none. |
| Starch agar | Growth: moderate, faint yellowish-orange, no soluble pigment. | Growth: moderate, orange, no soluble pigment. | Growth: moderate, ochre, no soluble pigment. |
| Tyrosine agar | Growth: poor, faint terra cotta, no soluble pigment. | Growth: poor, faint grayish-yellow to brown, no soluble pigment. | Growth: poor, faint grayish-yellow to brown, no soluble pigment. |
| Nutrient agar | Growth: moderate, faint beige, no soluble pigment. | Growth: moderate, faint beige, no soluble pigment. | Growth: moderate, faint beige, no soluble pigment. |
| Yeast extract-malt extract-agar | Growth: good, light orange to dull reddish-orange, no soluble pigment. | Growth: good, orange to dark orange, no soluble pigment. | Growth: good, dull orange, no soluble pigment. |
| Oat meal agar | Growth: none. | Growth: none. | Growth: none. |
| Bennett agar | Growth: moderate, light brown purple, no soluble pigment. | Growth: moderate, light brown purple, no soluble pigment. | Growth: moderate, light brown purple, no soluble pigment. |
| N-Z amine (1:1) agar | Growth: good, light brownish purple, no soluble pigment. | Growth: good, dull orange, no sluble pigment. | Growth: good, faint orange purple, no soluble pigment. |
| Emmerson agar | Growth: good, dull reddish orange, no soluble pigment. | Growth: good, light brown, no soluble pigment. | Growth: good, faint brown, no soluble pigment. |
| Egg-albumin agar | Growth: moderate, faint brown purple, no soluble pigment. | Growth: moderate, faint brown purple, no soluble pigment. | Growth: moderate, faint brown purple, no soluble pigment. |

III. Utilization of carbohydrates

The utilization of carbohydrates was examined in a Pridham-Gottlieb medium; results are shown in the following table 2.

IV. Physiological properties (observed after 2 week-incubation at 29° C.)

TABLE 3

|  | Micromonospora sp. K-6993 | Micromonospora sp. K-6993-Y-41 | Micromonospora echinospora NRRL 2985-N-6 |
|---|---|---|---|
| Liquefaction of gelatin | + | ± | + |
| Milk coagulation | − | − | − |
| Milk peptonization* | + | − | + |
| Cellulose decompo- | ± | −∼± | ± |

TABLE 3-continued

|  | Micromonospora sp. K-6993 | Micromonospora sp. K-6993-Y-41 | Micromonospora echinospora NRRL 2985-N-6 |
|---|---|---|---|
| sition* | | | |
| Nitrate reduction | + | ± | −∼± |
| Tyrosinase formation | − | − | − |

*observed after one month incubation at 37° C.

Micromonospora sp. K-6993 produce a single spore on substrate mycelia without producing aerial mycelia. Thus, it belongs to the Micromonospora species.

Gentamicin producing strains of Micromonospora species which have already been reported are listed as follows:

*Micromonospora purpurea* NRRL 2953.
*Micromonospora echinospora* var. *echinospora* NRRL 2985.
*Micromonospora echinospora* var. *ferruginea* NRRL 2995.
*Micromonospora echinospora* var. *pallida* NRRL 2996.

[These strains are described in Antimicrobial Agents and Chemotherapy. 116-124. (1963) and Published examined Japanese patent application No. 21934/1969.]

*Micromonospora sagamiensis* MK-65.
*Micromonospora sagamiensis* var. *nonreducans* MK-62.
*Micromonospora sagamiensis* var. *flava* Mm-628.

[These strains are described in Published examined Japanese patent applications No. 39155/1975 and No. 6755/1976.]

The characteristics of Micromonospora sp. K-6993 were compared with those of the above seven strains and the results are shown in table 4.

TABLE 4

|  | Nitrate reduction | Liquefaction of gelatin | Liquefaction of milk | Color of growth |
|---|---|---|---|---|
| *Micromonospora* sp. K-6993 | + | + | + | purple |
| *M. purpurea* | + | ± | + | dark purple |
| *M. echinospora* | ± | + | + | purple |
| *M. echinospora* var. *ferruginea* | − | + | + | " |
| *M. echinospora* var. *pallida* | + | + | + | orange |
| *M. sagami ensis* MK-65 | + | ± | + | " |
| *M. sagamiensis* var. *nonreducans* MK-62 | − | − | − | " |
| *M. sagamiensis* var. *flava* Mn-628 | − | ± | + | " |

As seen from the table, Micromonospora sp. K-6993 is a novel strain having some similarities to *Micromonospora echinospora*.

In order to convert Kanamycin A or Kanamycin B into the compounds of general formula (I), the above-mentioned strains are cultivated in the presence of Kanamycin A or Kanamycin B. In this invention, conventional cultivation methods for producing antibiotics are carried out. Various nutrients are used for the cultivation. As carbon sources, dextrose, starch, soluble starch, dextrin, sucrose, molasses, etc. can be used solely or in combination therewith, and hydrocarbons, alcohols, organic acids, animal and vegetable oils, etc., can be used according to the utilization capacity of strains. As nitrogen sources, inorganic salts such as ammonium chloride, ammonium sulfate, urea, ammonium nitrate, sodium nitrite, etc., natural nitrogen sources such as soybean meal, defatted soybean meal, cotton seed meal, gluten meal, corn meal, peptone, meat extract, yeast extract, dry yeast, corn steep liquor, etc., can be used solely or in combination therewith. And if necessary, amino acids, nucleic acids, vitamines, inorganic salts such as sodium chloride, calcium carbonate, phosphates, magnecium sulfate, cobalt chloride, etc., can be used.

As cultivation methods, a liquid culture, especially an aerated submerged culture is preferred. The temperature of the cultivation is 25°-45° C., preferably, 28°-32° C., and the preferred pH is about neutral. Of course, the cultivation conditions such as compositions of the medium, pH of the medium, temperature, agitation or aeration, etc., may be modified according to the strain used or the amount of Kanamycin added.

For producing the compounds of general formula (I), the starting material Kanamycin A or Kanamycon B is added to the medium at the start or within about 72 hours from the start of the cultivation. The amounts of Kanamycin A or Kanamycin B is about 0.1-10 g/liter and may be added in one time or in portionwise and it is used as it is or as its acid addition salt such as the sulfate. Cultivation is continued until the compounds of general formula (I) accumulate in the medium. It is usually 3 to 7 days after the addition of Kanamycin.

The amount accumulated is assayed on the ordinary paper disc method with *Escherichia coli* K-12 ML-1629 which is selectively sensitive to the compounds of general formula (I), but not to Kanamycins A and B.

For isolation and purification of the compounds of general formula (I) from cultivated broth, conventional methods used for aminoglycosides are applied. That is, absorption with cation and/or anion exchange resins, absorption with active charcoal, and cellulose and silica gel column chromatographies can be used solely or in combination thereof.

Practically, for example, after adjusting the pH of the culture solution from 2 to 3, mycelium is filtered off and the pH of the filtered broth is adjusted from 6 to 7, then the desired compound is absorbed on a resin having a carboxylic acid or sulfonic acid group which is suitable for absorbing and desorbing the desired compound, for example, a cation exchange resin, such as Amberlite IRC-50 (trade name) ($NH_4^+$), Dowex 50w (trade name) ($NH_4^{30}$) and the desired compound is eluted with 1 N ammonium hydroxide. The solution thus obtained is concentrated under reduced pressure and the residue is charged into Amberlite CG-50 (trade name) ($NH_4^+$) by continuous gradient elution technique using ammonium hydroxide. Further purification can be carried out by silica gel column chromatography, etc., and if necessary, by repeating column chronatography packed with Amberlite CG-50 ($NH_4^+$), Dowex (trade name) ($OH^-$), etc.

Typical examples of the compounds of general formula (I) obtained by the abovementioned method are as follows:

3''-N-Methyl-4''-C-methyl-3',4'-dideoxy-6'-N-methylkanamycin B or its 4''-epimer (I-B$_1$)

3''-N-Methyl-4''-C-methyl-3',4'-dideoxykanamycin B or its 4''-epimer (I-B$_2$)

3''-N-Methyl-4''-C-methyl-3',4'-dideoxy-6'-N-methylkanamycin A or its 4''-epimer (I-A$_1$)

3''-N-Methyl-4''-C-methyl-3',4'-dideoxykanamycin A or its 4''-epimer (I-A$_2$)

EXAMPLE 1

Preparation of the desired compound [I-B$_1$] by strain K-6993-Y-41

Into 100 ml of a liquid medium (pH 7.5) containing 5% dextrin, 3.5% skimmed soybean meal Esusanmito-Tokku (trade name) and 0.7% calcium carbonate in 500 ml flask was inoculated Micromonospora sp. strain K-6993-Y-41 which was cultivated on a modified Bennet's agar slant for 2 weeks at 30° C. The flask was shaken for 48 to 72 hours at 29° C. to provide a seed culture solution.

Separately, 100 ml of a main culture medium was prepared in a 500 ml flask and 1 ml of the above-described seed culture solution was inoculated to the culture medium. The main culture medium had the composition of 5% dextrin, 3.5% skimmed soybean meal Esusanmito-Tokkyu (trade name), 0.7% calcium carbonate, and 0.000025% cobalt chloride (pH 7.5) and was used after sterilization at 120° C. for 20 minutes. After cultivation for 24 hours, Kanamycin B was added to the culture medium in an amount of 300 mcg (potency) per milliliter of the medium. Thereafter, the shaking of the culture was performed for 120 hours at 29° C., whereupon the antimicrobial potency in the broth was measured by a paper disc method using *Escherichia coli* K-12 ML-1629 (polypeptone agar medium) and an inhibited zone of 15.5 mm diameter was observed. Then, the pH of 20 liters of the culture solution obtained was adjusted to 2.0 with 4 N hydrochloric acid, mycelia were filtered off. The pH of the filtered broth was readjusted to 7.0 with 4 N sodium hydroxide solution and the filtered broth was charged to a column packed with 1.6 liters of Amberlite IRC-50 (NH$_4^+$) to adsorb the desired compound (I-B$_1$). After washing the column with water, the product was eluted with 5 liters of 1 N ammonium hydroxide and the eluate was concentrated under reduced pressure and dried to provide 10.6 g of crude powder. The crude powder was adsorbed on 900 ml of Amberlite CG-50 (NH$_4^+$) column and after washing the resin with water, a continuous gradient elution was performed using 3.5 liters of water and 3.5 liters of 0.8 N ammonium hydroxide. Then, each fraction (15 ml each) was detected by a paper disc method using *Excherichia coli* K-12 ML-1629 as test strain and a silica gel thin layer chromatography [Kieselgel 60 F$_{254}$ of 0.25 mm thick, (trade name) made by Merck & Co.; developed for 2 hours with the developing solvent (A in Table 5); ninhydrin coloring Rf value 0.43]. The desired compound was eluted in the fractions of Fraction No. 270 to No. 310. The active fractions were collected, combined, concentrated under reduced pressure, preparatively chromatographed on a silica gel plate [Kieselgel 60 PF$_{254}$ (trade name) made by Merck & Co., 0.3 mm thick and 20×20 cm$^2$, activated for 5 hours at 150° C.] using the above-mentioned developing solvent. After development, the position of the desired compound was confirmed by ninhydrin coloring, the desired compound was scraped out together with silica gel, and the compound was extracted from the silica gel with the same developing solvent. The extract was concentrated under reduced pressure and then resubjected to column chromatography using 10 ml of Amberlite CG-50 (NH$_4^+$). Then, a continuous gradient elution was performed using 200 ml of water and 200 ml of 0.8 N ammonium hydroxide, and after confirming the active fractions thus emerged by means of the aforesaid silica gel thin layer chromatography, the fractions containing the desired compound were collected, concentrated, and lyophilized to provide 37 mg of white powder. After dissolving 37 mg of the white powder in 5 ml of methanol, the solution obtained was acidified by the addition of a 0.1 N sulfuric acid methanolic solution and the precipitates formed were recovered by filtration and dried in vacuum to provide the sulfate of the desired compound. The sulfate was dissolved in 0.5 ml of water, the solution was charged to a column packed with 10 ml of Dowex 1×2 (OH$^-$) and the column was eluted with water. The active fractions thus emerged were collected, concentrated under reduced pressure, charged on a column containing 10 ml of Amberlite CG-50 (NH$_4^+$), and then a continuous gradient elution was performed using 200 ml of water and 200 ml of 0.8 N ammonium hydroxide. After confirming the active fractions by the aforesaid silica gel thin layer chromatography, the fractions containing the desired compound were collected, concentrated under reduced pressure and lyophilized to provide 24 mg of the white powder of the pure desired compound [I-B$_1$].

The free base [I-B$_1$] (the lyophilized product) had the following physico-chemical properties:

(1) Basic white powder (vacuum-dried for 24 hours at 95° C.)

(2) Solubility: Very easily soluble in water; soluble in methanol and ethanol; sparingly soluble in acetone; and insoluble in chloroform, benzene, ethyl acetate, butyl acetate, ether, n-hexane, etc.

| (3) Elemental analysis for $C_{21}H_{43}N_5O_8 \cdot H_2O$: | | | |
|---|---|---|---|
| | C | H | N |
| Calculated: | 49.30% | 8.87% | 13.69% |
| Found: | 49.51% | 9.13% | 13.52% |

(4) Melting point: 108°–111° C.

(5) Optical rotation: $[\alpha]_D^{25} + 128°$ (C=1%, in H$_2$O)

Figure 1:
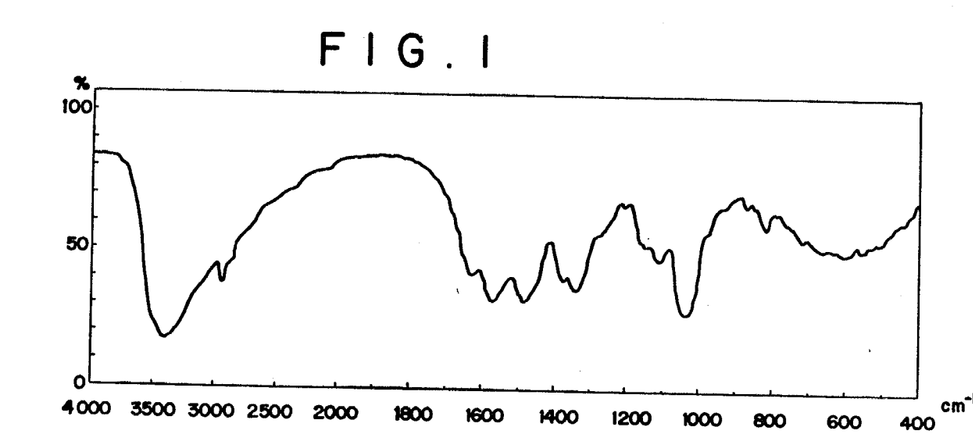
FIG. 1 and FIG. 2 show respectively infrared absorption spectra and nuclear magnetic resonance spectra of the desired compound [I-B$_1$] of this invention.

(6) Ultraviolet absorption spectrum: terminal absorption (7) Infrared absorption spectrum (KBr): FIG. 1, Maximum absorption (cm$^{-1}$): 1040, 1115, 1270, 1340, 1385, 1485, 1570, 1640, 2930, and 3390

Figure 2:
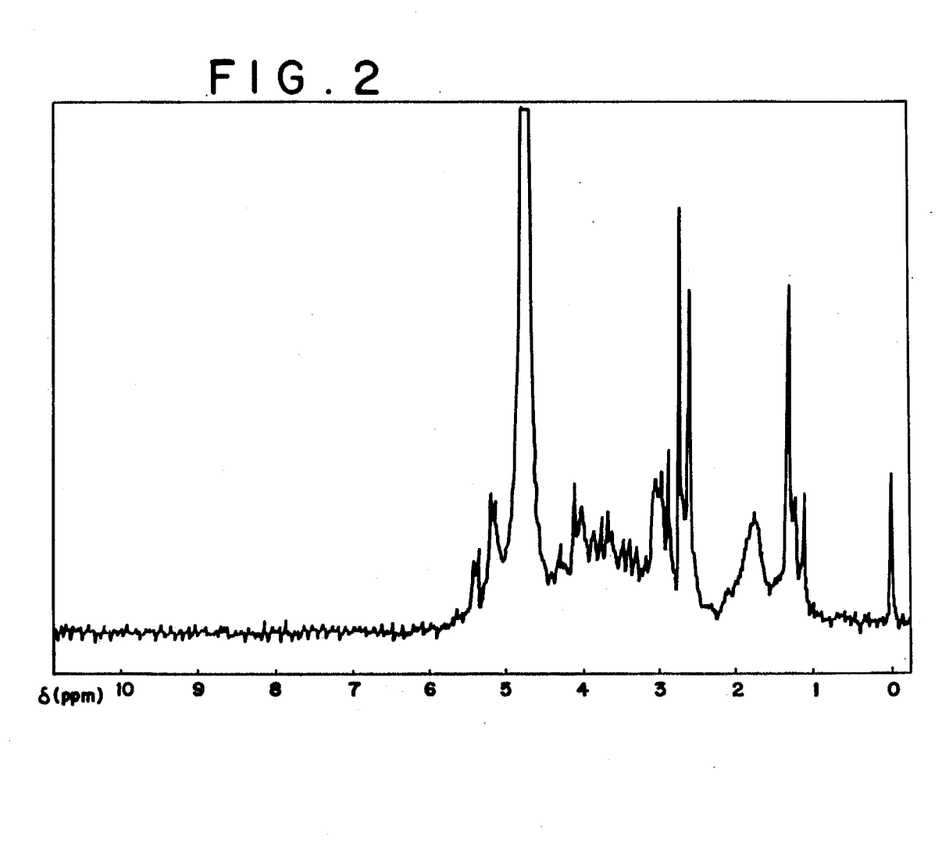

(8) NMR spectrum (in D$_2$O): FIG. 2, Characteristic peaks: 1.3 ppm—tertiary 4''-C-methyl, 2.6 ppm—6'-N-methyl, 2.7 ppm—3''-N-methyl, 5.12 ppm—1''-anomeric proton, 5.37 ppm—1'-anomeric proton.

(9) Mass spectrum: Main ion peaks (m/e): 112, 125, 143, 144, 172, 190, 330, 334, 352, 380, 393, 494 (M+1)

(10) Rf value by thin layer chromatography: Table 5

From the above physico-chemical properties, in particular the results by the mass spectrum and NMR (nuclear magnetic resonance spectrum) together with the charateristics of the starting material Kanamycin B, the compound thus obtained is confirmed to be 3″-N-methyl-4″-C-methyl-3′,4′-dideoxy-6′-methyl Kanamycin B or 4″-epimer thereof having the following formula:

In addition, as indicated by the above structure, the compound [I-B₁] inhibited the growth of the resistant bacteria which inactivate Kanamycin B and 3′,4′-dideoxy Kanamycin by acetylating the amino group at the 6′-position thereof, such as *Pseudomonas aeruginosa* GN 315, *Escherichia coli* K-12 R-5, etc.

EXAMPLE 2

Preparation of the desired compound by strain NRRL-2985-N-6

By employing the similar cultivation method, the culture media, the addition amount of Kanamycin B, the addition method thereof, etc., as in Example 1, 20 liters of a cultivated solution was obtained. The solution thus obtained was absorbed on Amberlite IRC-50 ($NH_4^+$) followed by desorption and after performing a gradient column chromatography using Amberlite CG-50 ($NH_4^+$), the fractions containing the desired compound [I-B₁] were collected, concentrated under reduced pressure, and subjected to silica gel thin layer chromatography as in Example 1, followed by a gradient chromatography of Amberlite CG-50 ($NH_4^+$) to provide 13 mg of the compound, [I-B₁] as the white powder. By treating the white powder as Example 1, 7 mg of the white powder of the pure desired compound [I-B₁] was obtained.

EXAMPLE 3

Preparation of the desired compound [I-B₂] by strain K-6993-Y-41

The seed culture cultivated as in Example 1 was inoculated and cultivated in a culture medium containing 1.5% soluble starch, 1.0% yeast extract, 0.3% Triptose (trade name, made by Difco Co.), 0.3% magnesium sulfate.7H₂O, 0.3% dipotassium hydrogenphosphate and 0.000025% cobalt chloride (pH 7.2). After 24 hours, Kanamycin B was added to become 300 mcg/ml and the shaking of culture was further continued for 115 hours at 29° C. After filtering 20 liters of the culture solution obtained as Example 1, the filtrate was charged to a column packed with 1.6 liters of Amberlite IRC-50 ($NH_4^+$) to adsorb the desired compound [I-B₂], which was then eluted with 5 liters of 1 N aqueous ammonia. By concentrating the eluate under reduced pressure, 12.1 g of a crude elution product was obtained. The crude elution product was adsorbed on 900 ml of Amberlite CG-50 ($NH_4^+$) packed in a column, a gradient elution was performed using 3.5 liters of water and 3.5 liters of 0.8 N aqueous ammonia, and fractions containing the desired compound showning Rf value of 0.36 on thin layer chromatography were collected as in Example 1. Then, after performing the silica gel preparative thin layer chromatography as in Example 1, the extract was subjected to a column chromatography using 20 ml of Amberlite CG-50 ($NH_4^+$) and a gradient elution was practiced using 300 ml of water and 300 ml of 0.8 N aqueous ammonia. Then, the fractions containing the desired compound were collected and lyophilized to provide 99 mg of white powder.

By treating 70 mg of the white powder as in Example 1, 45 mg of the white powder of the pure desired compound [I-B₂] was obtained.

The free base [I-B₂] (the lyophilized product) had the following physico-chemical properties:

(1) Basic white powder (dried in vacuum for 3 hours at 95° C.)

(2) Solubility: Very easily soluble in water, soluble in methanol; sparingly soluble in ethanol and acetone; and insoluble in chloroform, benzene, ethyl acetate, butyl acetate, ether, n-hexane, etc.

| (3) Elemental analysis for $C_{20}H_{41}N_5O_8 \cdot H_2O$: | | | |
|---|---|---|---|
| | C | H | N |
| Calculated | 48.28% | 8.71% | 14.07% |
| Found: | 48.06% | 8.96% | 14.11% |

(4) Melting point: 143°–146° C.

(5) Optical rotation: $[\alpha]_D^{25} + 142°$ (C=1%, in H₂O)

(6) Ultraviolet absorption spectrum: terminal absorption

Figure 3:
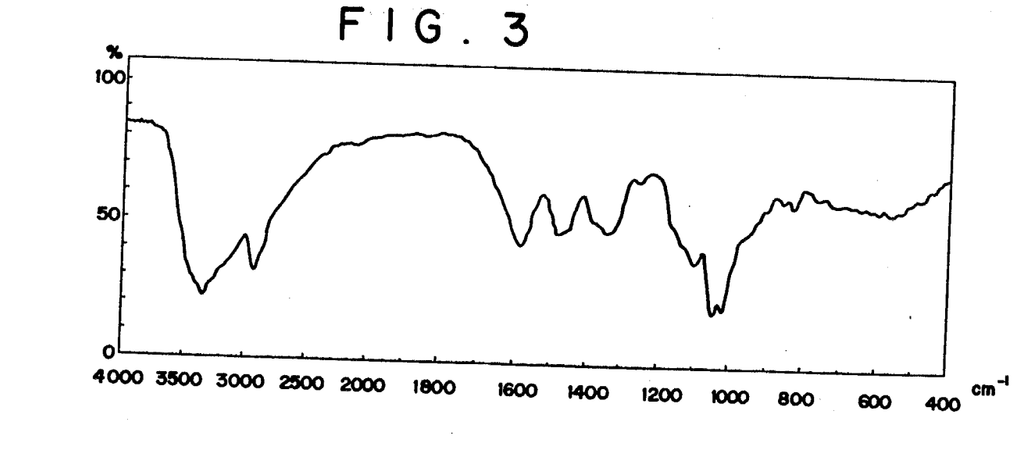
FIG. 3 and FIG. 4 show respectively infrared absorption spectra and nuclear magnetic resonance spectra of the desired compound [I-B$_2$] of this invention.

(7) Infrared absorption spectrum (KBr): FIG. 3, Maximum absorption ($cm^{-1}$): 1020, 1050, 1105, 1130, 1260, 1340, 1450, 1474, 1580, 2920, 3330

Figure 4:
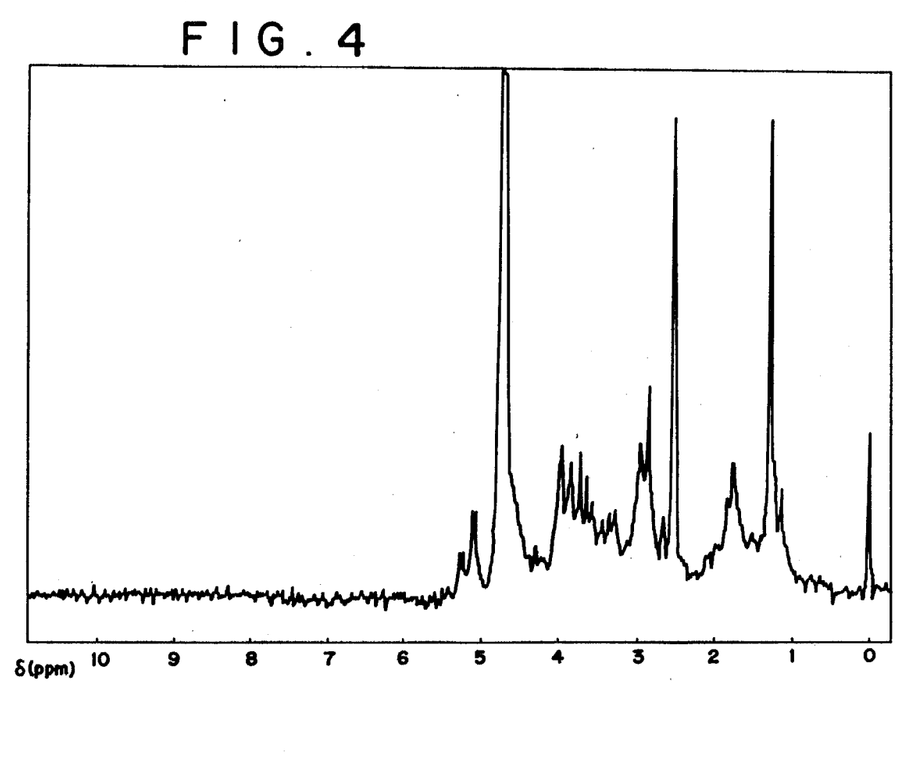

(8) NMR spectrum (in D₂O): FIG. 4, Characteristic peaks: 1.28 ppm—tertiary 4″-C-methyl, 2.55 ppm—3″-N-methyl, 5.09 ppm—1″-anomeric proton, 5.26 ppm—1′-anomeric proton.

(9) Mass spectrum: Main ion peaks (m/e): 112, 129, 144, 172, 190, 319, 334, 352, 380, 479, and 480 (M+1)

(10) Rf value of thin layer chromatography: Table 5

From the above-described physico-chemical properties, in particular the results of the mass spectrum and NMR, the compound [I-B₂] obtained was confirmed to be 3″-N-methyl-4″-C-methyl-3′,4′-dideoxy Kanamycin B or the 4″-epimer thereof shown by the following formula:

EXAMPLE 4

Preparation of the desired compound [I-B₂] by strain NRRL 2985-N-6

The similar cultivation method, culture media, addition amount and method of Kanamycin B, etc., as in Example 1 were employed in this example. Then, 20 liters of the culture solution obtained was adsorbed on Amberlite IRC-50 (NH$_4^+$) followed by desorption, a gradient column chromatography was performed using Amberlite CG-50 (NH$_4^+$) and the active fractions containing the desired compound [I-B₂] were collected and concentrated under reduced pressure. Then, preparative silica gel thin layer chromatography was performed as in Example 1 and further the active fractions were collected by a gradient chromatography using Amberlite CG-50 (NH$_4^+$) to provide 83 mg of the desired compound as the white powder. Then, by treating 80 mg of the compound as in Example 1, 51 mg of the white powder of the pure desired compound [I-B₂] was obtained.

EXAMPLE 5

Preparation of the desired compound [I-A₂] by strain K-6993-Y-41

By following the similar procedure as in Example 1 using the same cultivation method, culture media, addition amount and method of Kanamycin A, etc., 50 liters of a culture solution was obtained.

The culture solution thus obtained was charged to a column packed with 4 liters of Amberlite IRC-50 (NH$_4^+$) and, after washing the column with water, the column was eluted with 20 liters of 1 N aqueous ammonia. The eluate was concentrated under reduced pressure and lyophilized to provide 25.5 g of a crude elution product. The crude elution product was subjected to a gradient elution in a column packed with 1.6 liters of Amberlite CG-50 (NH$_4^+$) using 7 liters of water and 7 liters of 0.7 N aqueous ammonia. Then, the similar detection as in Example 1 was performed and the fractions containing the desired compound [I-A₂] was collected and concentrated under reduced pressure. The residue formed was applied to a silica gel column chromatography (Wako Gel C-200, trade name, 20 mm×900 mm) and eluted by the developing solvent A in Table 5, whereby the crude fractions of the desired compound [I-A₂] were obtained. For further purifying the crude fraction thus obtained, the preparative silica gel thin layer chromatography was carried out as in Example 1 and the crude desired compound thus obtained was subjected to a gradient chromatography in a column packed with 10 ml of Amberlite CG-50 (NH$_4^+$) using 100 ml of water and 100 ml of 0.7 N aqueous ammonia.

The fractions containing the desired compound were combined, concentrated under reduced pressure, and lyophilized to provide 35 mg of the desired compound [I-A₂] as the white powder thereof.

By treating similarly the powder as in Example 1, 13 mg of the pure desired compound [I-A₂] was obtained.

The free base [I-A₂] (the lyophilized product) had the following physicochemical properties:

(1) Basic white powder (vacuum-dried for 24 hours at 95° C.)

(2) Solubility: Very easily soluble in water; soluble in methanol; sparingly soluble in ethanol and acetone; and insoluble in chloroform, benzene, ethyl acetate, butyl acetate, ether, n-hexane, etc.

| (3) Elemental analysis for $C_{20}H_{40}N_4O_9 \cdot H_2O$: | | | |
|---|---|---|---|
| | C | H | N |
| Calculated: | 48.18% | 8.49% | 11.24% |
| Found: | 48.59% | 8.80% | 11.15% |

(4) Melting point: 129°–151° C.

(5) Optical rotation: $[\alpha]_D^{25} + 147.5$ (C=1%, in H$_2$O)

(6) Ultraviolet absorption spectrum: terminal absorption

Figure 5:
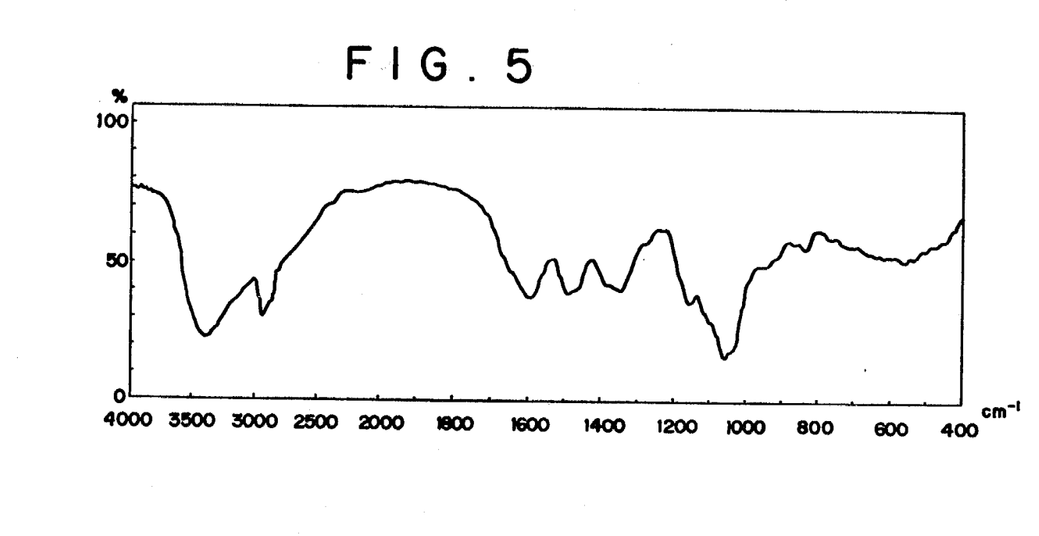
FIG. 5 and FIG. 6 show respectively infrared absorption spectra and nuclear magnetic resonance spectra of the desired compound [I-A$_2$] of this invention.

(7) Infrared absorption spectrum (KBr): FIG. 5 Maximum absorption (cm$^{-1}$): 820, 1025, 1050, 1090, 1145, 1260, 1330, 1365, 1455, 1475, 1580, 2925, and 3350.

Figure 6:
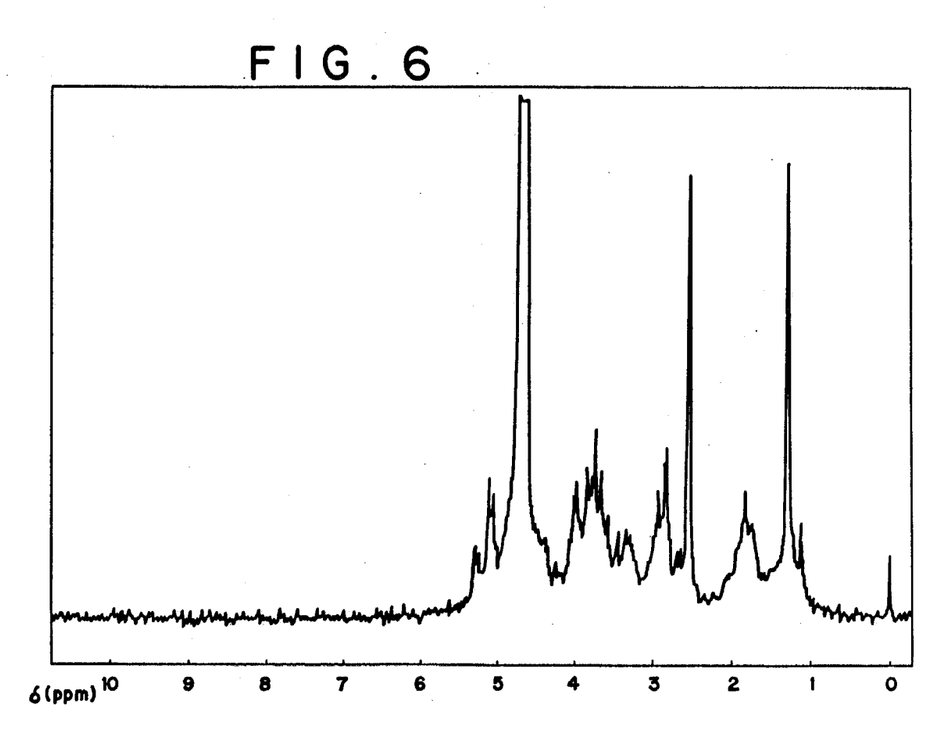

(8) NMR spectrum (in D$_2$O): FIG. 6 Characteristic peaks: 1.29 ppm—tertiary 4″-C-methyl, 2.56 ppm—3″-N-methyl, 5.12 ppm—1″-anomeric proton, 5.27 ppm—1′-anomeric proton, (9) Mass spectrum: Main ion peaks (m/e): 113, 130, 172, 190, 320, 334, 352, 362, 380, 480, and 481 (M+1)

(10) Rf value by thin layer chromatography: Table 5

From the above physico-chemical properties, in particular the results of the mass spectrum and NMR, the compound [I-A₂] obtained in this example was confirmed to be 3′-N-methyl-4″-C-methyl-3′,4′-dideoxy Kanamycin A or the 4″-epimer thereof shown by the following formula:

EXAMPLE 6

Preparation of the desired compound [I-A$_2$] by strain K-6993-Y-41

A medium containing 1.5% soluble starch, 1.0% yeast extract, 0.3% Triptose (trade name), 0.3% magnesium sulfate.7H$_2$O, 0.3% dipotassium hydrogenphosphate, and 0.000025% cobalt chloride (pH 7.5) was sterilized for 20 minutes at 120° C. and a seed culture similarly prepared as Example 1 and containing Kanamycin A sulfate at a concentration of 1000 mcg (potency) per ml was inoculated to the medium at 1% concentration. Then, 20 liters of the culture solution obtained by performing the shaking of culture for 144 hours at 29° C. was adsorbed on 1.8 liters of Amberlite IRC-50 (NH$_4$+) packed in a column as in Example 1 and after washing the column with water, the column was eluted with 1 N aqueous ammonia. The eluate obtained was concentrated under reduced pressure and lyophilized to provide 22.3 g of a crude elution product. The crude product was subjected to a gradient chromatography with 3.5 liters of water and 3.5 liters of 0.7 N aqueous ammonia using a column packed with 800 ml of Amberlite CG-50 (NH$_4$+) and the fractions containing the desired compound [I-A$_2$] which was detected by thin layer chromatography as in Example 1 were collected, concentrated under reduced pressure, applied to a silica gel column chromatography (Wako Gel C-200 of 20 mm×900 mm), then the column was eluted with the developing solvent A in Table 5, whereby the fractions containing the desired compound [I-A$_2$] were obtained. The detection of the fractions were performed using similar thin layer chromatography as in the above procedure. The fractions thus obtained were combined and subjected to a gradient chromatography again with the column containing 10 ml of Amberlite CG-50 (NH$_4$+) and the active fractions were collected and lyophilized to provide 28 mg of the desired compound [I-A$_2$]. By treating similarly the compound as in Example 1, 9 mg of the pure desired compound [I-A$_2$] was obtained.

In addition, the Rf values by thin layer chromatography of the desired compounds [I-B$_1$], [I-B$_2$], and [I-A$_2$] obtained in the above examples are shown in Table 5 together with those of known aminoglycoside antibiotics for comparison:

TABLE 5

|  | Rf value | |
|---|---|---|
|  | A | B |
| [I-B$_1$] | 0.43 | 0.09 |
| [I-B$_2$] | 0.36 | 0.05 |
| [I-A$_2$] | 0.39 | 0.06 |
| Gentamicin C$_1$ | 0.51 | 0.15 |
| Gentamicin C$_2$ | 0.47 | 0.12 |
| Gentamicin C$_1$[a] | 0.42 | 0.08 |
| Gentamicin C$_2$[b] (Sagamicin) | 0.47 | 0.12 |
| Sisomicin | 0.42 | 0.09 |
| Tobramycin | 0.08 | 0 |
| Kanamycin A | 0.04 | 0 |
| Kanamycin B | 0.05 | 0 |
| Neomycin B | 0.02 | 0 |
| Paromomycin | 0.03 | 0 |
| Ribostamycin | 0.05 | 0 |

Silica gel thin layer: Kieselgel 60H$_{254}$ (trade name, made by Merck) 20 × 20 cm, 0.25 mm
Developing solvent:
A chloroform: methanol: 28: aqueous ammonia (20:15:8)
B chloroform: methanol: 28% aqueous ammonia (2:1:1), lower phase

EXAMPLE 7 (Injection)

In 350 ml of distilled water for injection was suspended 25 mg of the compound [I-B$_1$] and the pH was adjusted to 7 by adding gradually 2 N sulfuric acid, distilled water for injection was further added to make 500 ml of the total solution. The solution was aseptically filtered and 5 ml of each of the solution was placed in each vial, lyophilized by an ordinary manner, and the vials were sealed.

EXAMPLE 8 (Tablet)

| Compound [I-B$_2$] | 500 g |
|---|---|
| Microcrystalline cellulose | 37 g |
| Light silicic anhydride | 12.5 g |
| Polysorbate 80 | 5 g |
| Carboxymethyl cellulose calcium | 40 g |

The above components were mixed and after further adding thereto a proper amount of water, the mixture was kneaded and sieved to form granules. The granules obtained were dispersed in 5.5 g of magnesium stearate and then 2000 tablet cores were prepared by an ordinary manner. Then, by applying glue coating, tablets each containing 250 mg of the compound [I-B$_2$] were obtained.

EXAMPLE 9 (Suppository)

After fusing 84 g of higher fatty acid triglyceride (Witepsol, trade name) at 45° C., 3.5 g of polyoxyethylene lauryl ether and 12.5 g of the compound [I-A$_2$] were dispersed therein with stirring. Then, 2.0 g each of the dispersion was poured into a mold for a suppository and after it solidified, the suppository formed was separated from the mold.

EXAMPLE 10 (Dry syrup)

A rough mixture of 78.6 g of a purified cane sugar powder and 20.0 g of the compound [I-B$_2$] prepared in a mixer was placed in a mortar and after adding thereto a binder solution prepared by dissolving 0.4 g of methyl p-oxybenzoate and 1.0 g of hydroxypropyl cellulose in 15.0 g of isopropanol, the mixture was kneaded well in the mortar. The kneaded mixture was passed through a 20 mesh sieve to form granules, which were dried in a dryer.

What is claimed is:

1. A process for producing aminoglycoside antibiotics represented by the formula wherein R$_1$ is a hydrogen atom or a methyl group and R$_2$ represents an amino group or a hydroxyl group, or their pharmacologically acceptable acid addition salts, which comprises cultivating a Gentamicin producing strain of Micromonospora species or a mutant thereof in a medium containing Kanamycin A or Kanamycin B.

2. A process of claim 1 wherein the Gentamicin producing strain of Micromonospora species is Micromonospora sp. K-6993.

3. A process of claim 1 wherein the mutant of the Gentamicin producing strain of Micromonospora species is Micromonospora sp. K-6993-Y-41.

4. A process of claim 1 wherein the mutant of Gentamicin producing strain of Micromonospora species is *Micromonospora echinospora* NRRL 2985-N-6.

* * * * *